United States Patent
Kogan et al.

(10) Patent No.: US 7,638,775 B2
(45) Date of Patent: Dec. 29, 2009

(54) METHODS AND SYSTEMS FOR REDUCING RADIATION ATTENUATION IN IMAGING SYSTEMS

(75) Inventors: Michael Kogan, Haifa (IL); Alexander Vaisburd, Haifa (IL); Danny Hausner, Haifa (IL)

(73) Assignee: General Electric Company, Schenectady, NY (US)

( * ) Notice: Subject to any disclaimer, the term of this patent is extended or adjusted under 35 U.S.C. 154(b) by 440 days.

(21) Appl. No.: 11/481,377

(22) Filed: Jul. 5, 2006

(65) Prior Publication Data
US 2008/0005839 A1   Jan. 10, 2008

(51) Int. Cl.
G01F 23/00   (2006.01)
(52) U.S. Cl. .................................. 250/370.09
(58) Field of Classification Search ............ 250/370.09; 378/195, 198
See application file for complete search history.

(56) References Cited

U.S. PATENT DOCUMENTS

| | | | | |
|---|---|---|---|---|
| 3,652,851 | A * | 3/1972 | Zaalberg ........................ 5/601 |
| 4,602,378 | A * | 7/1986 | Kelman et al. ................. 378/26 |
| 4,977,588 | A * | 12/1990 | Van der Ende .............. 378/196 |
| 5,029,826 | A * | 7/1991 | Schaefer ........................ 5/600 |
| 5,078,142 | A * | 1/1992 | Siczek et al. ................. 600/407 |
| 5,613,254 | A * | 3/1997 | Clayman et al. ............... 5/600 |
| 5,950,262 | A * | 9/1999 | Smoler et al. .................. 5/613 |
| 6,194,725 | B1 | 2/2001 | Colsher et al. |
| 6,237,172 | B1 * | 5/2001 | Morgan, Sr. ................... 5/618 |
| 6,298,506 | B1 * | 10/2001 | Heinold et al. ................. 5/613 |
| 6,357,066 | B1 | 3/2002 | Pierce |
| 6,446,286 | B1 * | 9/2002 | Karmalawy ..................... 5/601 |
| 6,886,198 | B2 * | 5/2005 | Marin et al. .................... 5/601 |
| 6,899,459 | B1 * | 5/2005 | McKenna ..................... 378/181 |
| 7,173,265 | B2 * | 2/2007 | Miller et al. ............. 250/492.3 |
| 7,242,002 | B2 * | 7/2007 | Blevis et al. ........... 250/363.05 |
| 7,288,759 | B2 | 10/2007 | Frangioni |
| 2002/0032927 | A1 * | 3/2002 | Dinkler ......................... 5/601 |
| 2004/0263865 | A1 | 12/2004 | Pawlak et al. |
| 2005/0055773 | A1 * | 3/2005 | Cooke ............................ 5/620 |
| 2005/0059877 | A1 | 3/2005 | Falbo |

(Continued)

FOREIGN PATENT DOCUMENTS

WO   WO 2005/018735 A2   3/2005

(Continued)

OTHER PUBLICATIONS c.cam A Whole New Angle in Cardiology, Siemens Medical, ©2005, 15 pgs.

*Primary Examiner*—Constantine Hannaher
*Assistant Examiner*—Djura Malevic
(74) *Attorney, Agent, or Firm*—The Small Patent Law Group; Dean D. Small

(57) ABSTRACT

Methods and systems for a patient table having a longitudinal axis for a medical imaging system are provided. The patient table includes a body including a first end, an axially-spaced second end, and a first and a second axially oriented side edges extending therebetween, the body further including at least one of an aperture extending through the body and a notch extending from at least one of the first and second axially oriented side edges, and a base configured to couple to the body using at least one of the first end and the second end.

20 Claims, 2 Drawing Sheets

U.S. PATENT DOCUMENTS

2006/0002511 A1 1/2006 Miller et al.
2006/0186622 A1 8/2006 Darling, III
2007/0039101 A1* 2/2007 Luginbuhl et al. ............. 5/600
2007/0237305 A1* 10/2007 Youngblood-Johnson ... 378/177

FOREIGN PATENT DOCUMENTS

WO    WO 2006/091239 A2    8/2006

* cited by examiner

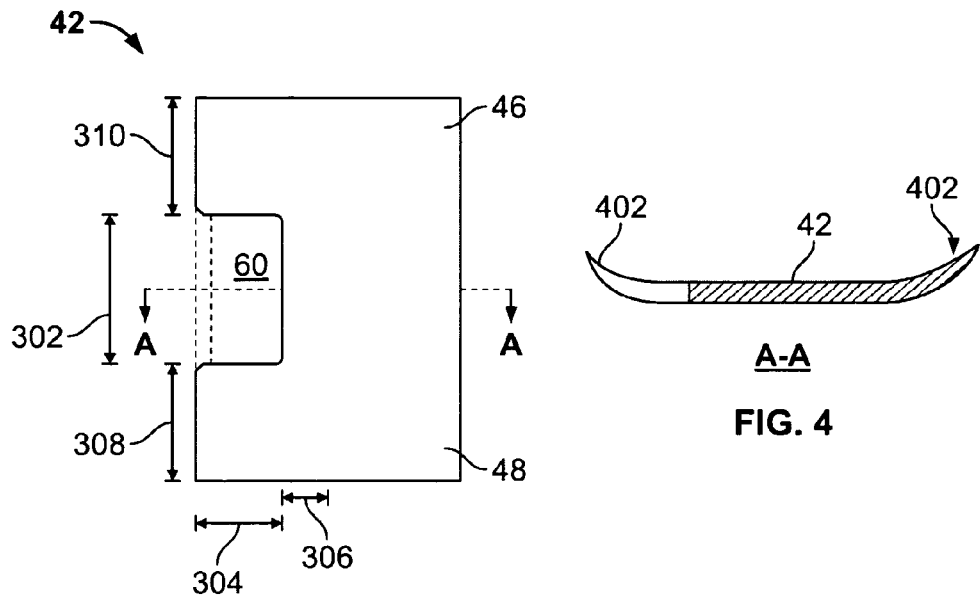
FIG. 3
FIG. 4
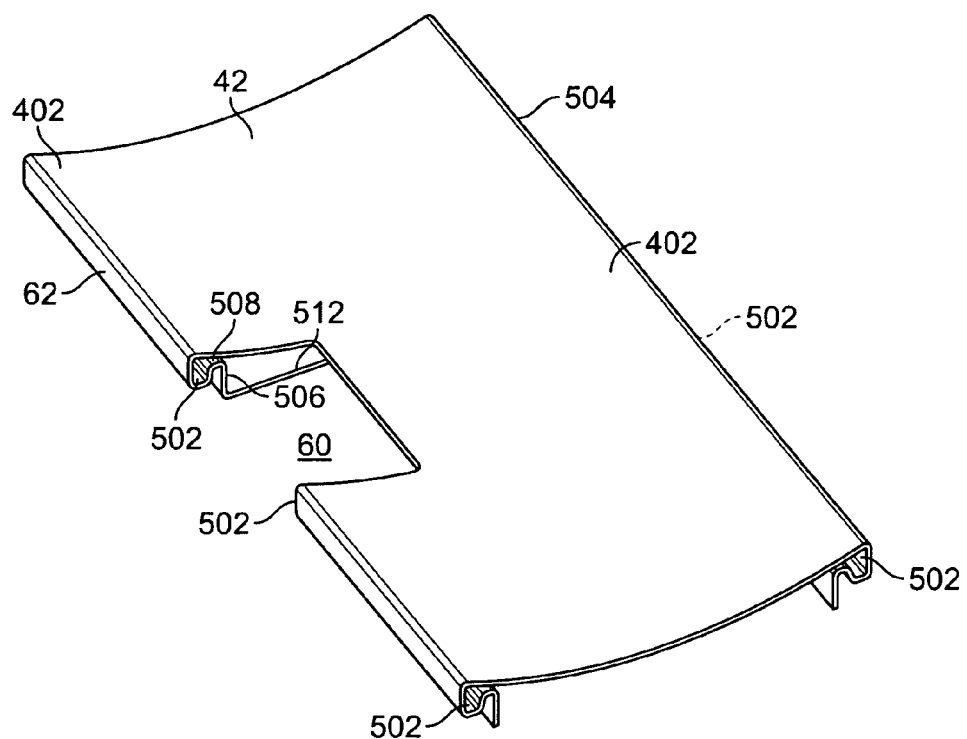
FIG. 5

METHODS AND SYSTEMS FOR REDUCING RADIATION ATTENUATION IN IMAGING SYSTEMS

BACKGROUND OF THE INVENTION

This invention relates generally to medical imaging systems and, more particularly, to a method of reducing radiation attenuation by imaging system hardware.

Medical imaging requires accurate and repeatable positioning of the patient for a scan and a table that facilitates minimizing attenuation of the gamma radiation. Attenuation of the gamma radiation for example, in the table material of cardiac cameras, increases the examination duration and negatively affects the image quality. Specifically, in a cardiac camera, low energy radiation is emitted. During a scan the patient heart may be located on a left-side or a right-side of the table based on the patient position being supine or prone.

BRIEF DESCRIPTION OF THE INVENTION

In one embodiment, a patient table having a longitudinal axis for a medical imaging system includes a body including a first end, an axially-spaced second end, and a first and a second axially oriented side edges extending therebetween, the body further including at least one of an aperture extending through the body and a notch extending from at least one of the first and second axially oriented side edges, and a base configured to couple to the body using at least one of the first end and the second end.

In another embodiment, a method of imaging a patient using a patient table is provided. The patient table includes a base portion and a body including a notch that is at least one of open to a side edge of the body and closed to a side edge of the body, the body configured to couple to the base. The method includes determining a patient orientation for an imaging scan, if the patient is to be scanned in a supine orientation, coupling the body to the base in a first position such that the notch is adjacent a region of interest of the patient, and if the patient is to be scanned in a prone orientation, coupling the body to the base in a second position such that the notch is adjacent the region of interest of the patient.

In yet another embodiment, an imaging system includes a radiation source, a detector configured to receive radiation from the source, and a patient table that includes a body including a first end, an axially-spaced second end, and a first and a second axially oriented side edges extending therebetween, the body further including at least one of an aperture extending through the body and a notch extending from at least one of the first and second axially oriented side edges, and a base configured to couple to the body using at least one of the first end and the second end.

BRIEF DESCRIPTION OF THE DRAWINGS

FIG. 3 is a top view of the second portion shown in FIG. 2;
FIG. 4 is a cross-sectional view of second portion taken along line A-A shown in FIG. 3;
and
FIG. 5 is a perspective view of an exemplary embodiment of the second portion shown in FIG. 2.

DETAILED DESCRIPTION OF THE INVENTION

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Figure 1:
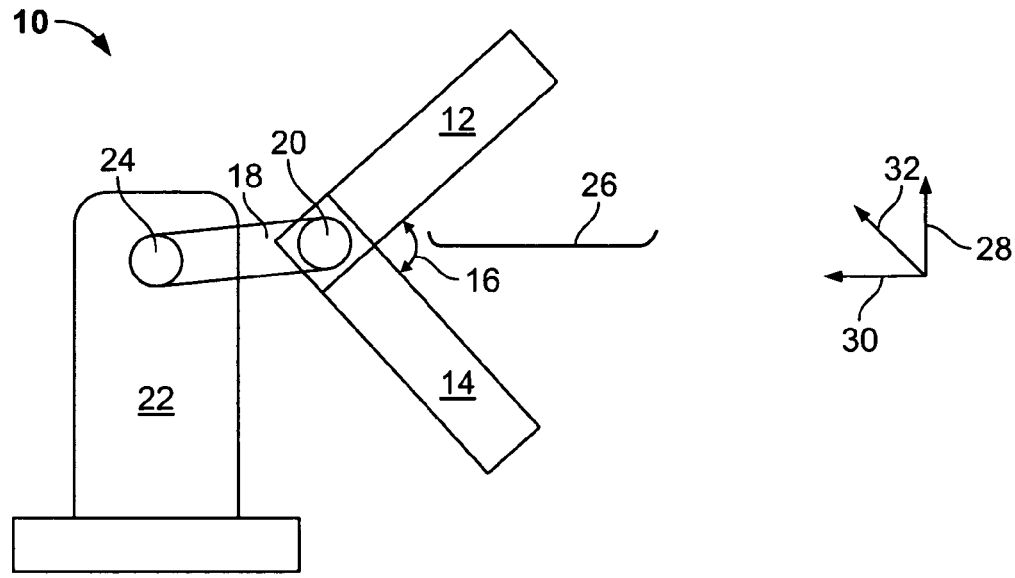
FIG. 1 is an end view of an exemplary imaging system.

FIG. 1 is an end view of an exemplary imaging system 10. In the exemplary embodiment, imaging system 10 is an emission nuclear imaging system and includes a first nuclear detector 12, for example, a gamma camera and a second nuclear detector 14. Detectors 12 and 14 are fixed at a relative angle 16 of approximately ninety degrees. In an alternative embodiment, angle 16 is selectively adjustable. Detectors 12 and 14 are coupled to a support arm 18 through a first rotatable joint 20. Support arm 20 is coupled to a base 22 through a second rotatable joint 24. In an alternative embodiment, additional support arms and rotatable joint are coupled between detectors 11 and 12. and base 22 such that detectors 11 and 12 may be articulated in a plurality of orientations. A patient table 26 is positioned within a field of view (FOV) of detectors 11 and 12. Patient table 26 is configured to be selectively adjustable in a vertical direction 28, a lateral direction 30, and an axial direction 32. Patient table 34 is also configured to incline about a selectable axis along a longitudinal axis 36 of table 34.

Figure 2:
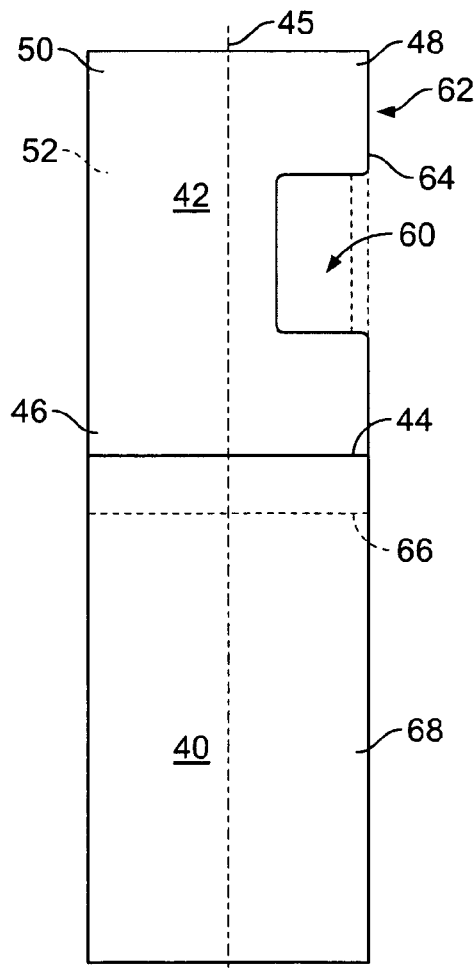
FIG. 2 is a top view of an exemplary patient table that may be used with imaging system shown in FIG. 1.

FIG. 2 is a top view of an exemplary patient table 26 that may be used with imaging system 10 (shown in FIG. 1). Patient table 26 includes a first portion 40 and a removable second portion 42 coupled to first portion 40 at a joint 44 aligned along a longitudinal axis 45. A mechanical interface of second portion 42 to first portion 40 is substantially identical in a supine position and in a prone position of the patient such that second portion 42 may be coupled to first portion 40 using either end of second portion 42 so that the notch is oriented on a left side or a right side of the table according to the patient (prone or supine) position. A first end 46 of second portion 42 is configured to be substantially identical to a second end 48 of second portion 42 such that second portion 42 may be uncoupled from first portion 40, rotated one hundred eighty degrees, and recoupled to first portion 40. In an alternative embodiment, a top surface 50 of second portion 42 is configured to be substantially identical to a bottom surface 52 of second portion 42 such that second portion 42 may be rotated one hundred eighty degrees about longitudinal axis 45.

Second portion 42 includes a cutout area or notch 60 extending along a side 62 of second portion 42 making it axially asymmetrical in a patient heart area. In the exemplary embodiment, notch 60 extends to an edge 64 of side 62. In an alternative embodiment, notch 60 does not extend to edge 64, but rather forms an aperture through second portion 62. A depth of notch 60 is predetermined such that in all positions of detectors 12 and 14 during a scan, the gamma rays emitting from the organ are received by detectors 12 and 14 while avoiding attenuation in table 26.

First portion 40 includes a bendable joint 66 configured to control an angle between a top surface 68 of first portion 40 and a top surface 60 of second portion 42. For example, a patient seated on first portion 40 may have their upper body inclined with respect to their lower body by adjusting the angle between top surface 68 and top surface 50 using bendable joint 66. The patient may also be reclined to a prone or supine position using joint 66.

During scanning a patient may be positioned on table 26 in a seated and/or reclining position. Second portion may be oriented with top surface 50 facing vertically upward such that notch 60 is located on the patient's left side when in a supine position on table 26. Notch 60 is aligned substantially with an organ of interest, for example, the patient's heart such that radiation emitted from the organ does not pass through table 26 before being received by detected 12 and/or 14. When the patient is positioned on table 26 in a prone position, second portion 42 is rotated one hundred eighty degrees such that notch 60 is located on an opposite side of table 26 to align with an organ on the left side of the patient in a prone position, for example, the heart.

In each position of notch 60, table 26 axial dimension ensures location of the patient organ proximate a central area of notch 60 while the patient head is located adjacent to distal end 48.

Notch 60 facilitates reducing average examination time and improving image quality in both the supine and prone patient positions. Absorption of table material in a conventional table is approximately 10%-20%. Accordingly, a scan time saving of approximately 10%-20% is realizable using table 26 with notch 60.

FIG. 3 is a top view of second portion 42 (shown in FIG. 2). Second portion 42 is illustrated with notch 60 on the left side of a patient positioned on table 26 in a prone position. Notch 60 includes an axial length 302 and a depth 304 with respect to side 64. An offset 306 from longitudinal axis 45 furthers defines the boundaries of notch 60. Side 64 may be closed such that an aperture is formed rather than a notch open to side 64. In the exemplary embodiment, a first axial dimension 308 defines a distance from second end 48 to an edge of notch 60 and a second axial dimension 310 defines a distance from first end 46 to an edge of notch 60. When first axial dimension 308 is substantially equal to a second axial dimension 310 notch 60 is axially aligned with the same area of the patient when the patient is laying supine and when laying prone.

FIG. 4 is a cross-sectional view of second portion 42 taken along line A-A (shown in FIG. 3). In the exemplary embodiment, second portion 42 includes an upwardly curved lip 402 configured to cradle the patient and provide stiffening support of second portion 42 along its axial length.

FIG. 5 is a perspective view of an exemplary embodiment of second portion 42 (shown in FIG. 2). In the exemplary embodiment, second portion 42 includes notch 60 and a stiffening channel 502 extending along side 62 and an opposing side 504. Stiffening channel 502 is coupled to a first end 508 of a downwardly extending rib 506. A second opposite end 510 of rib 506 is coupled to a bottom plate 512.

The above-described embodiments of a medical imaging system provide a cost-effective and reliable means for minimizing attenuation of radiation by a patient table. The table is configured to also provide ergonomic and comfort features to ease the anxiety of patients and expedite scanning by technicians.

Exemplary embodiments of medical imaging systems and apparatus are described above in detail. The medical imaging system components illustrated are not limited to the specific embodiments described herein, but rather, components of each system may be utilized independently and separately from other components described herein. For example, the medical imaging system components described above may also be used in combination with different medical imaging system components.

A technical effect of the various embodiments of the systems and methods described herein include facilitating operation of the medical imaging system by providing patient support and comfort that is compatible with a zero attenuation of the camera radiation during a scan. Specifically, the patient table provides a notch in the heart area of the patient regardless of the patient's supine or prone position. The notch provides a zero table attenuation.

While the invention has been described in terms of various specific embodiments, those skilled in the art will recognize that the invention can be practiced with modification within the spirit and scope of the claims.

What is claimed is:

1. A patient table having a longitudinal axis for a medical imaging system comprising:
    a removable body comprising a first end, an axially-spaced second end, and first and second axially oriented side edges extending therebetween, said body further comprising at least one cut-out extending through said body; and
    a base supporting said body and having a joint configured to couple to said body, wherein each of said first and second ends of said body is configured to separately couple to said joint, said base and said body extending along the longitudinal axis when coupled together to support a patient thereon.

2. A patient table in accordance with claim 1 wherein said body further comprises:
    a first surface extending between said first and second ends and said first and a second side edges; and
    a second surface extending between said first and second ends and said first and a second side edges, said first and second surfaces facing in opposite directions;
    wherein said body is configured to separately couple to said joint in different first and second orientations, the patient resting upon said first surface when said body is in said first orientation and the patient resting upon said second surface when said body is in said second orientation.

3. A patient table in accordance with claim 1 wherein said body has an arcuate cross-section extending between said first and second side edges.

4. A patient table in accordance with claim 1 wherein said cut-out is substantially centered between said first and second ends.

5. A patient table in accordance with claim 1 wherein said cut-out has a predetermined spatial location that corresponds to a region of interest in the patient when the patient is lying upon said body.

6. A patient table in accordance with claim 1 wherein said base further comprises a bendable joint that extends along a lateral axis of said base, the lateral axis extending perpendicular to the longitudinal axis and along a surface of the base, said bendable joint rotating about the lateral axis to move said body between reclined and inclined positions.

7. A patient table in accordance with claim 1 wherein said first end and said joint couple together at a first mechanical interface and said second end and said joint couple together at a second mechanical interface, said first and second ends being substantially identical so that said first and second mechanical interfaces are substantially identical.

8. A patient table in accordance with claim 1 wherein said body further comprises a pair of stiffening channels formed by said body, each stiffening channel extending along the longitudinal axis and along a corresponding side edge.

9. A patient table in accordance with claim 1 wherein said cut-out is at least one of an aperture and a notch through said body, said notch extending from and opening to one of said first and second side edges.

10. A patient table in accordance with claim 1 wherein said body is configured to support an upper body of the patient and said base is configured to support a lower body of the patient.

11. A patient table in accordance with claim 1 wherein at least one of said first and second ends of said body is configured to separately couple to said joint to hold said body in different first and second orientations, said body having a surface extending between said first and second ends and said first and second side edges, the patient resting upon said surface when said body is in said first and second orientations.

12. A method of imaging a patient using a patient table including a base and a removable body having a cut-out, the body being supported by the base and configured to couple to a joint of the base such that the base and body extend along a longitudinal axis, said method comprising:
    determining a patient position for an imaging scan including one of a supine position and a prone position;
    if the patient is to be scanned in the supine position, coupling the body to the joint in a first orientation such that the cut-out has a first spatial location adjacent to a region of interest of the patient; and
    if the patient is to be scanned in the prone position, coupling the body to the joint in a different second orientation such that the cut-out has a different second spatial location adjacent to the region of interest of the patient.

13. A method in accordance with claim 12 further comprising:
    uncoupling the body from the joint of the base;
    rotating the body one hundred eighty degrees about the longitudinal axis to move the body between the first and second orientations; and
    coupling the body to the joint of the base, wherein the body has axially-spaced apart first and second ends, only one of the first and second ends being coupled to the joint in both of the first and second orientations.

14. A method in accordance with claim 12 wherein the body has axially-spaced apart first and second ends, further comprising:
    uncoupling the body from the joint of the base;
    rotating the body one hundred eighty degrees about a vertical axis extending through a center of the body to move the body between the first and second orientations; and
    coupling the body to the joint of the base, the first end of the body being coupled to the joint in the first orientation and the second end of the body being coupled to the joint in the second orientation.

15. A method in accordance with claim 12 further comprising moving the body about a bendable joint of the base between reclined and inclined positions, the bendable joint extending along a lateral axis that is perpendicular to the longitudinal axis and along a surface of the base the patient rests upon.

16. An imaging system comprising:
    a radiation source;
    a detector configured to receive radiation from said source; and
    a patient table comprising:
        a removable body comprising a first end, an axially-spaced second end, and first and second axially oriented side edges extending therebetween, said body further comprising a cut-out extending through said body; and
        a base supporting said body and having a joint configured to couple to said body, wherein each of said first and second ends of said body is configured to separately couple to said joint, said base and said body extending along the longitudinal axis when coupled together to support a patient thereon.

17. An imaging system in accordance with claim 16 wherein said joint of said base is configured to couple to said first end and said second end of said body in a substantially identical manner.

18. An imaging system in accordance with claim 16 wherein said body further comprises:
    a first surface extending between said first and second ends and said first and a second side edges; and
    a second surface extending between said first and second ends and said first and a second side edges, said first and second surfaces facing in opposite directions;
    wherein said body is configured to be separately coupled to said joint in different first and second orientations, the patient resting upon said first surface when said body is in said first orientation and the patient resting upon said second surface when said body is in said second orientation.

19. An imaging system in accordance with claim 16 wherein said body has an arcuate cross-section that extends between said pair of side edges.

20. An imaging system in accordance with claim 16 wherein said cut-out is substantially centered between said first and second ends and proximate to one of said first and second side edges.

* * * * *

UNITED STATES PATENT AND TRADEMARK OFFICE
CERTIFICATE OF CORRECTION

PATENT NO.       : 7,638,775 B2                                    Page 1 of 1
APPLICATION NO.  : 11/481377
DATED            : December 29, 2009
INVENTOR(S)      : Kogan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this

Ninth Day of November, 2010

David J. Kappos
*Director of the United States Patent and Trademark Office*